United States Patent [19]

Campbell et al.

[11] 4,290,967

[45] Sep. 22, 1981

[54] PROCESS FOR RECOVERY OF PALLADIUM FROM NUCLEAR FUEL REPROCESSING WASTES

[75] Inventors: David O. Campbell, Oak Ridge; Samuel R. Buxton, Wartburg, both of Tenn.

[73] Assignee: The United States of America as represented by the United States Department of Energy, Washington, D.C.

[21] Appl. No.: 159,892

[22] Filed: Jun. 16, 1980

[51] Int. Cl.³ .......................... C01G 55/00; G21F 9/04
[52] U.S. Cl. .................................. 260/429 R; 423/22; 252/301.1 W
[58] Field of Search ........... 260/429 R; 252/301.1 W; 423/22; 75/101 BE

[56] References Cited

U.S. PATENT DOCUMENTS

| | | | |
|---|---|---|---|
| 3,716,605 | 2/1973 | Grimes et al. | 423/625 |
| 3,848,048 | 11/1974 | Moore | 252/301.1 W |
| 4,162,231 | 7/1979 | Horwitz et al. | 423/22 |

FOREIGN PATENT DOCUMENTS 996839 6/1965 United Kingdom ........ 252/301.1 W

*Primary Examiner*—Jacqueline V. Howard
*Attorney, Agent, or Firm*—Stephen D. Hamel; Richard G. Besha; James E. Denny

[57] ABSTRACT

Palladium is selectively removed from spent nuclear fuel reprocessing waste by adding sugar to a strong nitric acid solution of the waste to partially denitrate the solution and cause formation of an insoluble palladium compound. The process includes the steps of:

(a) adjusting the nitric acid content of the starting solution to about 10 M, (b) adding 50% sucrose solution in an amount sufficient to effect the precipitation of the palladium compound, (c) heating the solution at reflux temperature until precipitation is complete, and (d) centrifuging the solution to separate the precipitated palladium compound from the supernatant liquid.

8 Claims, 1 Drawing Figure

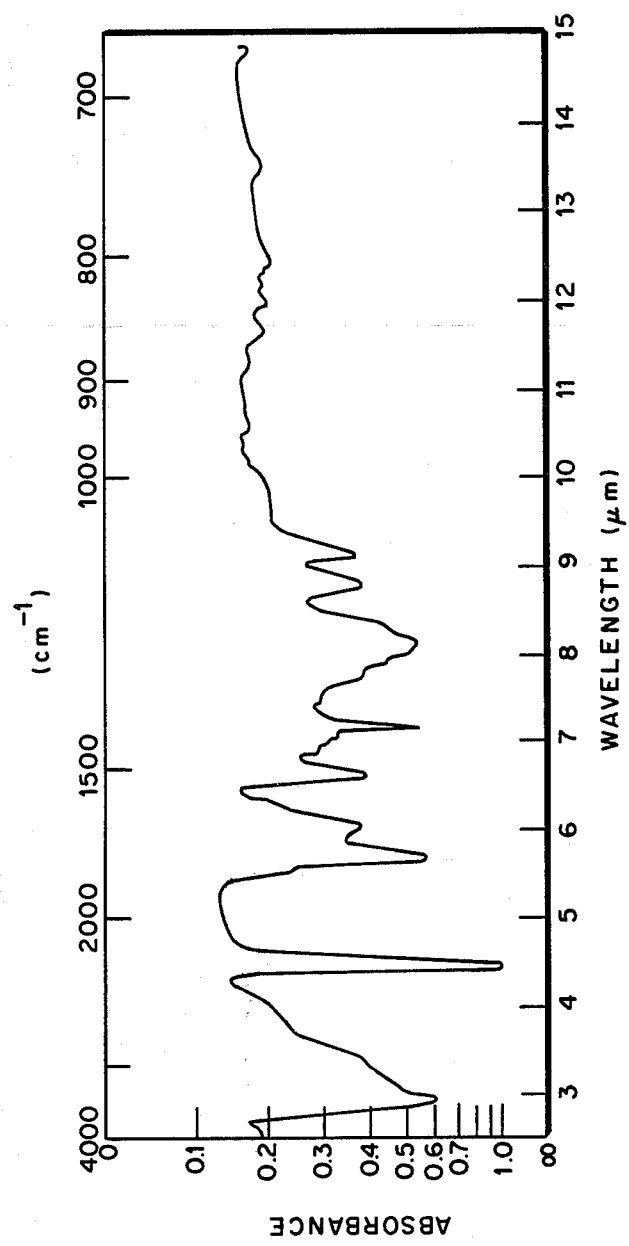

4,290,967

PROCESS FOR RECOVERY OF PALLADIUM FROM NUCLEAR FUEL REPROCESSING WASTES

Technical Field

This invention was made in the course of or under a contract with the Energy Research and Development Administration.

It relates to the art of nuclear fuel reprocessing and more particularly to the art of recovering palladium values from fission product waste solution.

In nuclear fuel reprocessing systems, spent fuel elements are periodically removed from the reactor prior to separation of fission products from fissionable uranium, plutonium and neptunium. The component containing the fission products generally leaves a first extractor as a nitric acid solution containing a variety of metal ions. The term "fission product waste solution" means a solution of the various metal ions remaining in solution following dissolution of spent nuclear fuel elements in acid and selective extraction of fissionable materials therefrom. The solution can contain useful radioisotopes, including $^{137}$Cs and $^{90}$Sr. Precious metals such as palladium, ruthenium and rhodium are present in quantities which make recovery economically worthwhile. Projected estimates of the production of nuclear waste from nuclear power reactors indicate that recovery of the palladium content of these wastes could possibly fulfill total needs of the U.S. for palladium.

Palladium has many industrial applications, including use as an emission control catalyst for automobile exhausts. The United States presently must import palladium, primarily from Russia, to meet growing needs for this metal. Development of domestic sources of palladium is not only attractive economically, but also may become essential to assure uninterrupted availability of this critically needed metal regardless of political turmoil elsewhere in the world.

In most fuel reprocessing plants, for example the Midwest Fuel Recovery Plant in Morris, Illinois, fuel rods are removed from their assemblies, cut to the desired length and fed to a continuous leacher, in which they are dissolved in nitric acid. The resulting solution is separated from the metal hulls, etc. and transferred to an extraction column in which it is contacted with a solvent (typically tributyl phosphate in an organic diluent) which selectively extracts the U, Pu and Np values from the solution. The extractant solution is then treated by well-known processes to further separate and recover the fissionable material. Typical examples are the Purex process, the "25" process, and the Butex process, as described in *Chemical Processing of Reactor Fuels*, Academic Press, New York and London (1961), incorporated herein by reference. The Purex process and other nuclear fuel reprocessing processes producing waste suitable for the practice of this invention are also more fully described in *Engineering For Nuclear Fuel Reprocessing*, Justin T. Long, Gordon and Breach Science Publishers, New York, London and Paris (1967) pp. 162-236, herein incorporated by reference.

The aqueous nitric acid solution (raffinate) remaining in the extraction column contains the fission products. The fission product solution is typically withdrawn from the extractor and subjected to further treatment before long-term storage.

BACKGROUND ART

It has been proposed by Campbell (U.S. Pat. No. 3,979,498), herein incorporated by reference, to recover palladium and cesium values from nuclear fuel reprocessing wastes by oxidation of Pd ions to Pd(IV) and treatment with chloride ions to cause precipitation of $Cs_2PDCl_6$, which can be removed.

Campbell et al have proposed, in U.S. Pat. No. 4,025,602, incorporated herein by reference, to recover transuranium elements from nuclear reactor waste by precipitation of lanthanide and actinide oxalates and subjecting the supernatant solution to treatment with a strong acid ion exchange resin to cause loading of lanthanide and actinide values on the resin.

A process in which a nitric acid solution of nuclear wastes is decomposed by sugar has been proposed by Bray et al, Invention Report HW-75565, "Use of Sugar to Neutralize Nitric Acid Waste Liquors," General Electric Co., Hanford Atomic Products Operation, Richland, Wash., Nov. 11, 1962, incorporated herein by reference. In this process, nuclear waste solution containing 5-10 M nitric acid is denitrated with sugar to an acid concentration of about 0.5 M. The solution is then neutralized with sodium hydroxide and made alkaline for long-term storage in tanks. Under these conditions, most of the fission products are precipitated along with metals such as iron. The recovery of palladium from the much larger amounts of other solids is therefore prohibitively expensive.

It will be appreciated that despite availability of a domestic source of palladium in the form of effluent from nuclear fuel reprocessing plants, there is presently no simple efficient and economical process for selective recovery of urgently needed palladium values therefrom.

DISCLOSURE OF INVENTION

It is the object of this invention to provide a simple, clean-cut and economical process for selectively removing palladium values from fuel-free nuclear waste reprocessing effluents.

This invention relates to a method for selective removal of palladium from a nitric acid solution of nuclear fuel reprocessing wastes, from which fuel values have been removed, comprising the steps of:

(a) adjusting the concentration of nitric acid in the solution to 8-12 M, (b) adding to the resulting 8-12 M nitric acid solution a mono- or disaccharide in an amount sufficient to react with palladium contained in the solution, (c) heating the resulting mixture containing mono- or disaccharide under reflux until precipitation of a palladium-containing solid ceases, and (d) separating the palladium-containing solid from a supernatant liquid.

In another aspect, this invention relates to a novel palladium containing solid of emperical formula $Pd_{1.1}C_{2.1}H_{4.1}N_2O$, obtained by the foregoing method.

BRIEF DESCRIPTION OF THE DRAWING

The drawing shows the infra-red spectrum of the palladium-containing solid obtained in accordance with the invention.

BEST MODE OF CARRYING OUT THE INVENTION

The solution from which the palladium is being recovered is typically the waste from spent nuclear fuel reprocessing from which fuel values have been removed, such as the raffinate from extraction with a blend of tributyl phosphate and solvent. The nitric acid concentration will vary according to the treatment previously received by the solution and must be adjusted to 8–12 M, preferably about 9–11 M. If denitration with sugar is done at lower nitric acid concentrations, interfering solid products are formed. These solids include a compound of zirconium and molybdenum which precipitates upon heating of solutions at acid concentrations of 4–5 M or less. Rare earth oxalates, formed by combination with the oxalate resulting from sugar decomposition, are insoluble in and will precipitate from solutions of low acid concentration. However, at extremely high acid concentrations, alkaline earth (barium and strontium) nitrates become increasingly insoluble and will precipitate. Also, the sugar decomposition product thought to precipitate palladium may be decomposed at very high nitric acid concentrations.

In the second step of the process, sugar is added as a 40–60% aqueous solution of sugar or as a solid sugar. The amount of sugar required is at least 100 times the weight of palladium in solution initially, a great excess over the stochiometric ratio for a reaction between sugar and palladium. The amount of palladium in the solution can be determined by spectrographic analysis or other conventional methods. The excess sugar is necessary because almost all of it reacts with nitric acid; only a small fraction forms the solid compound with palladium. Sugars thought to be effective in this process include the mono- and disaccharides, of which sucrose, fructose, maltose and dextrose are preferred.

The time required for precipitation of palpadium-sugar compound depends on the nature of the starting solution and the amount of palladium contained therein. These conditions may also affect the reflux temperature. Completeness of palladium precipitation can be determined by spectographic examination of a sample of the supernatant liquid for the absence of Pd ions or by any other method which will detect soluble palladium compounds.

The precipitated palladium compound has been partially characterized and appears to be a compound of palladium with a product or products from the decomposition of sugar by nitric acid. The compound is crystalline and has an x-ray diffraction pattern previously unreported in the literature. It is stable in common solvents, including organic solvents and all concentrations of HCl, $HNO_3$, NaOH or $Na_2CO_3$, as well as in other common acids and bases. It is soluble in highly concentrated solutions of $NH_4OH$ and KCN, which is consistent with knowledge that ammonia and $CN^-$ form complexes with palladium.

The palladium compound recovered from a synthetic waste solution, by refluxing with sugar in the presence of a high $HNO_3$ concentration, has an empirical formula of $Pd_{1.1}C_{2.1}H_{4.1}N_2O$ and has a tetragonal crystal structure.

The infrared spectrum is consistent with that of a mixture of two compounds or of a bridged structure having different binding groups. Fragments evolved during TGA and DTA analysis include those with m/z of 44 ($CO_2$) and 52 ($C_2N_2$).

Isolation of the insoluble palladium compound or complex from the nitric acid-sugar solution following refluxing can be done by conventional methods, including filtration and centrifugation.

When analysis of the resulting mother liquor or supernatant liquid indicates that removal of palladium from the solution is incomplete, it is possible to isolate additional compound from palladium and the decomposition product from the sugar-nitric acid reaction by adding additional mono- or disaccharide to the liquid and repeating the steps of heating under reflux and separating the thus-formed solid. Utilization of the process of this invention will therefore permit recovery of 90–99% of the palladium present in nuclear fuel processing wastes.

The recovered insoluble palladium compound or complex can be treated by conventional methods for recovery of palladium. See for example, Encyclopedia of Chemical Technology, 2nd ed. (Wiley, 1968), Vol. 15 at 846.

Preferably, the method of this invention is that wherein the concentration of nitric acid in the solution is adjusted to 9–11 M in step (a) and wherein the mono- or disaccharide is dextrose or sucrose.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight. The values obtained in elemental analyses are within commonly accepted limits of error.

EXAMPLE 1

Fully irradiated PWR (pressurized water reactor) fuel from the H. B. Robinson reactor was dissolved in 7 M $HNO_3$ to yield a solution containing about 350 g/l of uranium. The solution was extracted with tributyl phosphate to remove the uranium and plutonium. A nitric acid solution of fission products remained. The foregoing operations are analogous to the Purex process and produce a solution typical of high activity waste (HAW), which is the feed for the palladium recovery process.

A 100 ml sample of the HAW solution prepared as described above, and 80 ml of concentrated $HNO_3$ were charged to a 300 ml three-necked flask. The solution was distilled and condensate (50 ml) collected. Small amounts of solids from fission products may be present in the solution at this point. The solids are predominantly zirconium compounds, but if excess acid is not used, large amounts of zirconium molybdate would precipitate. The solution was bright red in color during the distillation.

The position of the condenser was changed so the solution could be heated under reflux instead of distilled. After addition of seven milliliters of a 50% sugar (sucrose) solution, the mixture was heated under reflux for 4 hours to form a cloudy liquid containing a precipitate. An additional 2 ml of 50% sugar solution was added and the solution was allowed to stand overnight at room temperature.

The next morning, the mixture was heated under reflux for 2 hours and centrifuged after being cooled to near room temperature. The recovered solid collected weight 24.2 mg. The solid contained 50% by weight Pd, 5 to 10% Rh, 5% Zr, and 1% other metals according to spectographic analysis. The supernatant liquid was sampled and analyzed by spark source mass analysis, which indicated that nearly one-half the palladium had been removed.

The supernatant liquid (120 ml) was returned to the flask. After addition of 4 g of dry sugar, the solution was heated under reflux for 5 hours. A precipitate appeared after about 1 hr. and increased in volume subsequently. The solution was centrifuged to permit recovery of 32.3 mg of solid. The solid contained 70% Pd and 1% any other metal. The supernatant liquid was sampled and analyzed as above; approximately 10% of the palladium remained.

Samples of both solids were examined and found to be generally similar in appearance and properties to the palladium compound made from synthetic waste (below).

(a) Analysis of the palladium-containing solids indicated the following elemental composition:

|    | Wt %  | Method |
|----|-------|--------|
| $N_2$ | 14.49 | (CHN analyzer) |
| C  | 12.99 | " |
| H  | 2.29  | " |
| O  | 8.28  | (Neutron activation, Nitrox-6) |
| Pd | 60.4  | (TGA, IDSSMS) |
| Loss on drying | 2.9 | |
| Empirical formula: $Pd_{1.1}C_{2.1}H_{4.1}N_2O$ | | |

(b) Exact mass measurement mass pyrograms showed that the m/z 44 evolved is $CO_2$ and that the m/z 52 is $C_2N_2$.

(C) IR: Numerous bonds between 2.9 and 9.2 um, but the spectrum differed from that of palladium cyanide. See drawing.

(d) X-ray diffraction showed that the compound has a tetragonal crystal structure
$a_o = 9.93 Å$,
$C_o = 7.96 Å$ (e) A sample dissolved in $NH_4OH$ was analyzed by NMR. No protonbearing species was observed. However, labile protons would be obscured by the OH and NH bonds and anything with a chemical shift near that of water would not be detected.

(f) A sample was dissolved in $NH_3-H_2O$ and then acidified. The resulting solution was converted to a trimehtylsilyl derivative by reaction with bis(-trimethylsilyl) -trifluoroacetamide (BSTSA) and analyzed by mass spectrometry. The data obtained from this solution indicate the sample is a lactone-type compound.

(g) Precipitates were prepared from the $HNO_3$-sucrose solution using Ni, Ag, and copper. Only the silver compound had a C N bond in the infrared (IR data). Gas evolution data and infrared spectra indicate that the Pd compound is either two compounds or a bridged structure with different binding groups.

EXAMPLE 2

A synthetic waste was prepared by dissolving the indicated elements in nitric acid to concentrations (grams/liter) indicated:

| Element | Quantity (g/l) | Compound | Remarks |
|---------|----------------|----------|---------|
| Sr | 0.263 | $Sr(NO_3)_2$ | Dissolved in water |
| In | 0.0004 | $In(NO_3)_3 \cdot 4H_2O$ | Dissolved in 1 M $HNO_3$ |
| Cd | 0.027 | Metal | Dissolved in 8 M $HNO_3$ |
| Cs | 0.780 | $CsNO_3$ | Dissolved in 0.1 M $HNO_3$ |
| Se | 0.016 | $H_2SeO_3$ | Dissolved in 2 M $HNO_3$ |
| Ba | 0.536 | $Ba(NO_3)_2$ | Dissolved in water |
| Te | 0.181 | Metal | Dissolved in 8 M $HNO_3$ |
| Mo | 1.10 | $(NH_4)_6Mo_7O_{24} \cdot 4H_2O$ | Dissolved in 0.5 M $HNO_3$ |
| Sn | 0.016 | Metal, granular (30 mesh) | Dissolved in 4 M $HNO_3$, no heat, no stirring |
| Ag | 0.019 | $AgNO_3$ | Dissolved in water |
| Zr | 1.17 | $ZrO(NO_3)_2 \cdot 2H_2O$ | Dissolved in 1 M $HNO_3$ |
| Br | 0.005 | $NaBrO_3$ | Dissolved in water |
| I | 0.086 | $HIO_3$ | Dissolved in water |
| As | 0.00003 | Metal | Dissolved in 8 M $HNO_3$ |
| Sb | 0.004 | Metal | Dissolved in 8 M $HNO_3$ |
| Pd | 0.456 | Metal | Dissolved in 8 M $HNO_3$, 3 drops HCl, boiled off chloride |
| Rh | 0.125 | Metal | Dissolved in a sealed tube containing HCl at high pressure, converted to nitrate by precipitating the chloride |
| Rb | 0.107 | RbCl | Dissolved in water, precipitated chloride with $AgNO_3$ |
| Ru | 0.688 | $RuCl_3$ | Dissolved in 4 M HCl, reduced acidity by heat and dilution, precipitated chloride with $AgNO_3$ |
| La | 0.410 | $La(NO_3)_3 \cdot 6H_2O$ | Dissolved in water |
| Y | 0.151 | $Y(NO_3)_3 \cdot 4H_2O$ | Dissolved in 0.5 M $HNO_3$ |
| Nd | 1.32 | $Nd_2(CO_3)_3$ | Dissolved in 2.0 M $HNO_3$ |
| Pr | 0.386 | $Pr(NO_3)_3 \cdot 5H_2O$ | Dissolved in 1 M $HNO_3$ |
| Ce | 0.796 | $Ce(NO_3)_3 \cdot 6H_2O$ | Dissolved in 1 M $HNO_3$ |
| Sm | 0.286 | $Sm_2O_3$ | Dissolved in 12 M $HNO_3$, evaporated to near dryness, added water |
| Gd | 0.038 | $Gd_2O_3$ | Dissolved in 12 M $HNO_3$ evaporated to near dryness, added water |
| Eu | 0.055 | $Eu_2O_3$ | Dissolved in 12 M $HNO_3$, evaporated to near dryness, added water |

The combined solution typically prepared in 5-10 liter batches, had a nitric acid concentration of about 2 M. Portions of this stock solution were used in each of a series of experiments. The acidity was increased by adding concentrated $HNO_3$; sugar was added as the solid or as a 50% solution, typically using 4 g sucrose per 100 ml of solution. The solution was then refluxed for about 4 hours. This resulted in removal of 90% of the Pd from the solution. The precipitated palladium complex, removed by centrifugation gave analytical results similar to those of Example 1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method for selective removal of palladium from a nitric acid solution of nuclear fuel reprocessing wastes, from which fuel values have been removed, comprising the steps of:
   (a) adjusting the concentration of nitric acid in the solution to 8–12 M,
   (b) adding to the resulting 8–12 M nitric acid solution a mono- or disaccharide in an amount sufficient to react with palladium contained in the solution,
   (c) heating the resulting mixture containing mono- or disaccharide under reflux until precipitation of a palladium-containing solid ceases, and
   (d) separating the palladium-containing solid from a supernatant liquid.

2. The method of claim 1, wherein the concentration of nitric acid in the solution is adjusted to 9–11 M in step (a).

3. The method of claim 1, wherein the mono- or disaccharide is sucrose in an excess of at least 100 times that required to react with the palladium contained in the solution.

4. The method of claim 1, wherein the mono- or disaccharide is dextrose in an excess of at least 100 times that required to react with the palladium contained in the solution.

5. The method of claim 1, including the further step of adding to the supernatant liquid of step (d) additional mono- or disaccharide, heating the resulting mixture under reflux to cause precipitation of a palladium-containing solid and isolating the palladium-containing solid.

6. The method of claim 1, wherein the concentration of nitric acid in the solution is adjusted to 9–11 M in step (a) and the mono- or disaccharide in sucrose in an excess of at least 100 times that required to react with the palladium contained in the solution.

7. The method of claim 1, wherein the concentration of nitric acid in the solution is adjusted to 9–11 M in step (a) and the mono- or disaccharide is dextrose in an excess of at least 100 times that required to react with the palladium contained in the solution.

8. A palladium-containing solid, prepared by the process of claim 1 and having the empirical formula $Pd_{1.1}C_{2.1}H_{4.1}N_2O$.

* * * * *